United States Patent [19]

Faler et al.

[11] 4,346,247

[45] * Aug. 24, 1982

[54] METHOD AND CATALYST FOR MAKING BISPHENOL

[75] Inventors: Gary R. Faler; George R. Loucks, both of Scotia, N.Y.

[73] Assignee: General Electric Company, Schenectady, N.Y.

[ * ] Notice: The portion of the term of this patent subsequent to Oct. 13, 1998, has been disclaimed.

[21] Appl. No.: 286,492

[22] Filed: Jul. 24, 1981

Related U.S. Application Data

[63] Continuation-in-part of Ser. No. 103,095, Dec. 13, 1979, Pat. No. 4,294,995.

[51] Int. Cl.$^3$ .................. C07C 37/00; C08F 112/08
[52] U.S. Cl. .............................. 568/728; 521/32; 568/727
[58] Field of Search .................... 568/727, 728

[56] References Cited

U.S. PATENT DOCUMENTS

| | | | |
|---|---|---|---|
| 2,923,744 | 2/1960 | Scriabine et al. | 568/728 |
| 3,394,089 | 7/1968 | McNutt et al. | 568/728 |
| 4,053,522 | 10/1977 | McClure et al. | 568/728 |
| 4,191,843 | 3/1980 | Kwantes et al. | 568/728 |
| 4,294,995 | 10/1981 | Faler et al. | 568/728 |
| 4,308,404 | 12/1981 | Kwantes et al. | 568/727 |
| 4,308,405 | 12/1981 | Kwantes | 568/727 |
| 4,319,053 | 3/1982 | Heuser et al. | 568/727 |

FOREIGN PATENT DOCUMENTS

| | | |
|---|---|---|
| 589727 | 10/1960 | Belgium . |
| 23325 | 7/1980 | European Pat. Off. . |
| 2733537 | 2/1978 | Fed. Rep. of Germany . |
| 2931036 | 2/1981 | Fed. Rep. of Germany . |
| 1185102 | 3/1970 | United Kingdom . |

Primary Examiner—Natalie Trousof
Assistant Examiner—Vera C. Clarke
Attorney, Agent, or Firm—William A. Teoli; James C. Davis, Jr.

[57] ABSTRACT

A sulfonated polystyrene ion-exchange resin is provided having organo mercaptan groups attached to backbone sulfone radicals by covalent nitrogen-sulfur linkages. The ion-exchange resin can be used to effect phenol-ketone condensation in the synthesis of bisphenols.

2 Claims, No Drawings

METHOD AND CATALYST FOR MAKING BISPHENOL

CROSS REFERENCE TO RELATED APPLICATIONS

This application is a continuation-in-part of application Ser. No. 103,095, filed Dec. 13, 1979, now U.S. Pat. No. 4,294,995.

BACKGROUND OF THE INVENTION

Prior to the present invention various methods were employed to synthesize bisphenols, such as bisphenol-A, by effecting reaction between a ketone and a phenol. One procedure, for example, involved the use of large amounts of inorganic acid catalysts, such as sulfuric acid or hydrochloric acid. Experience has shown, however, that the use of inorganic acids requires a means to neutralize such acids at the end of the reaction due to the corrosive action of the strong acids. In addition, distillation of the resulting bisphenol was often required because of the many by-products formed during the reaction under high acid conditions.

An improved procedure was developed by using a solid resin cation-exchange catalyst to effect the condensation between the phenol and the ketone. However, the disadvantage of the ion-exchange catalyst is the low acid concentration it provides resulting in the need for a rate accelerator such as a mercaptan. One procedure is shown by Apel et al, U.S. Pat. No. 3,153,001, which incorporates the mercaptan by partial neutralization of the ion-exchange catalyst in the form of a sulfonated insoluble polystyrene resin. Another procedure involves the partial esterification of such sulfonic acid moiety with an alkyl mercapto alcohol, as shown by McNutt et al, U.S. Pat. No. 1,183,564. A further procedure is shown by Wagner et al, U.S. Pat. No. 3,172,916, based on the partial reduction of the sulfonic acid to afford thiophenol functional groups. It has been found, however, that Wagner et al does not afford a particularly active type of promoter for synthesizing bisphenols, such as bisphenol-A, while the methods of Apel et al and McNutt et al are susceptible to chemical degradation.

Statement of the Invention

The present invention is based on the discovery that an N-organo aminodisulfide of the formula,

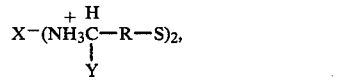 (1)

can be used to incorporate covalently bonded organo mercaptan groups into the backbone of the sulfonated polyaromatic organic polymer. There is obtained an ion-exchange resin having organo mercaptan groups covalently attached to sulfone radicals by nitrogen-sulfur linkages. An organo mercaptan activated sulfonated aromatic ion-exchange resin is formed capable of resisting the effects of the organo mercaptan degradation normally shown by the organo mercaptan sulfonated aromatic ion-exchange resins of the prior art. It has been found that after chemical attachment of the organo aminodisulfide of formula (1), the polymer can be reduced with a triorgano phosphine whereby the disulfide is converted to the mercaptan after acidification, where X of formula (1) is a halogen radical, or a counterion such as sulfate, etc., R of formula (1) is a divalent $C_{(1-13)}$ organo radical selected from aliphatic radicals and aromatic radicals and Y is a monovalent radical selected from hydrogen, carboxy, nitrile, etc.

There is provided by the present invention, an ion-exchange resin comprising a sulfonated polyaromatic organic material having from about 5 to about 25 mole percent of chemically combined organo mercaptan sulfonated aromatic organic units of the formula,

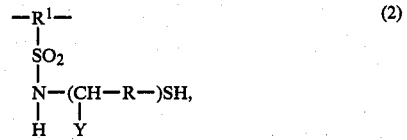 (2)

based on the total moles of chemically combined aromatic organic units in the material, where R and Y are as previously defined, and $R^1$ is a trivalent $C_{(6-13)}$ aromatic organic radical.

As utilized in the description of the present invention, the term "sulfonated polyaromatic organic material" signifies either a sulfonated polyaromatic organic polymer consisting essentially of chemically combined formula (2) units and formula (3) units and formula (4) units defined below, or a blend of such sulfonated polyaromatic organic polymer and an organic polymer consisting essentially of only formula (3) units and formula (4) units.

A further aspect of the present invention is directed to a method of making an organomercaptan sulfonated aromatic organic polymer which comprises, effecting reaction between (A) a halosulfonated aromatic organic polymer, and (B) an aminodisulfide of formula (1) in the presence of base, (ii) treating the resulting mixture of (i) with an effective amount of tri-organo phosphine which is sufficient to convert the disulfide of formula (1) to a mercaptan linkage of formula (2) and (iii) recovering the resulting organo mercaptan sulfonated aromatic organic polymer having chemically combined units of formula (2).

Halosulfonated aromatic organic polymer which can be utilized in the practice of the method of the present invention consists essentially of 5 to 95 mole percent of divalent $C_{(6-13)}$ aromatic organic units of the formula,

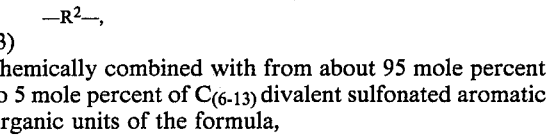

chemically combined with from about 95 mole percent to 5 mole percent of $C_{(6-13)}$ divalent sulfonated aromatic organic units of the formula,

 (4)

where $X^1$ is a halogen radical, for example chloro.

In a further aspect of the present invention, there is provided a method for making bisphenol which prior to the present invention was based on the reaction between a ketone and a phenol in the presence of effective amount of an insoluble strong acid cation-exchange resin in acid form modified by the neutralization of 5–25% of a cation-exchange capacity with a promoter in the form of an organo mercapto amine, whereby the promoter is incorporated onto the cation-exchange resin backbone by an acid-amine salt ionic bond which is susceptible to excessive loss from the cation-exchange resin due to leaching as the result of the degradation of the acid-amine salt ionic bond during the use of the ion-exchange resin in the phenol-ketone condensation reaction, the improvement which comprises utilizing as the cation-exchange resin, an insoluble strong acid polymer having 5–25% of its cation-exchange capacity occupied by a $C_2$–$C_{14}$ organo mercapto amine covalently bonded to the cation-exchange backbone by nitrogen-sulfur linkages.

There are included by the divalent $C_{(1-13)}$ organo radicals of R of formulas (1) and (2) alkylene radicals, for example, methylene, ethylene, propylene, butylene, pentylene, etc.; aromatic radicals, for example, phenylene, xylylene, tolylene, naphthylene, etc. In addition, R also includes substituted alkylene and arylene radicals as previously defined, such as halosubstituted, for example, chloro, fluoro, etc. Included within the radicals of $R^1$ and $R^2$ are, for example, divalent radicals and trivalent radicals such as

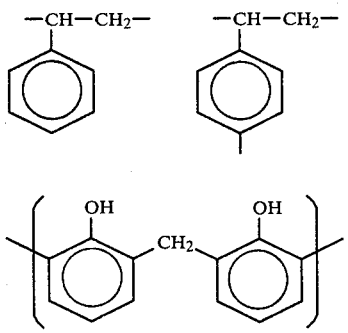

Phenols which can be used in the practice of the present invention in the above-identified method for making bisphenols are, for example, phenol and substituted phenols, such as

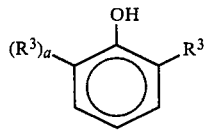

where $R^3$ is a $C_{(1-4)}$ alkyl radical, for example, methyl, ethyl, etc., and a is equal to 0 or 1.

Typical of the triorganophosphines which can be used in the practice of the invention are, for example, $$(R^4)_3P, \qquad (5)$$

where $R^4$ is selected from a $C_{(4-8)}$ alkyl radical or $C_{(6-13)}$ aryl radical. Some of the triorganophosphines included with formula (5) are, for example, tri-n-butyl phosphine, triphenylphosphine, etc.

Ketones which can be employed in the practice of the present invention to make the aforementioned bisphenols are, for example, acetone, diethyl ketone, methylethyl ketone, cyclohexanone, etc.

Halo sulfonated aromatic organic polymers having formula (3) and formula (4) units which can be modified in accordance with the practice of the present invention with N-organoamino disulfide of formula (1) are, for example, Amberlite-118, manufactured by Rohm and Haas Company, Dowex 50W X4, manufactured by Dow Chemical Company, etc., and other sulfonated polystyrenes which have been crosslinked with divinylbenzene.

The modification of the above-described ion-exchange resin with the N-organo amino disulfide of formula (1) can be accomplished in accordance with the following reaction

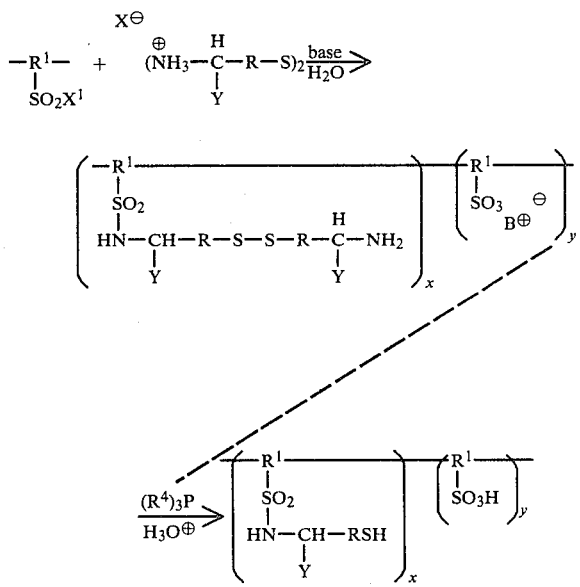

where R, $R^1$, $R^2$, X, $X^1$ and Y are as previously defined and x and y are mole percent ranges within the scope of the present invention and B is a base counterion such as sodium.

In the preparation of the mercaptan substituted sulfonated aromatic organic polymer, the halo sulfonated aromatic organic polymer can be contacted with N-organo amine disulfide of formula (1) in the presence of a suitable solvent and a base to produce a disulfide adduct of the aromatic sulfonated organic polymer. Suitable solvents which can be used, for example, are water, methanol, ethanol, etc. Bases which can be used in the formation of the disulfide adduct are tertiary organic amines such as triethylamine, pyridine, 4-(N-dimethyl amino)-pyridine, trimethylamine, etc. The proportions of the N-organo amino disulfide of formula (1) which can be employed will depend on the mole percent substitution of the halosulfonyl radicals on the backbone of the aromatic organic polymer. It has been found that effective results can be achieved if sufficient disulfide is employed to provide at least 0.1 to 2 equivalents of nitrogen per equivalent of halosulfonyl of the ion-exchange resin. Temperatures during the addition reaction can be 50° to 100° C. along with a sufficient agitation to facilitate reaction. If desired, an alkali metal carbonate or bicarbonate, such as sodium bicarbonate, can be employed as the base in place of the tertiary organic amine which would simultaneously effect adduct addition while neutralizing the excess unreacted halogen on the halosulfonyl radicals.

The reduction of cation-exchange resin disulfide atoms can be achieved by the use of a triorganophosphine by mixing the adduct with the triorganophosphine. A preferred procedure is to add the triorganophosphine in the form of an organic solvent solution to a mixture of the disulfide adduct in an aqueous organic solvent. The resulting mixture can thereafter be stirred under ambient conditions for several hours. The resulting reaction mixture can then be filtered and the recovered ion-exchange resin reaction product can be washed with an alkanol such as methanol, a suitable organic solvent, for example, methylene chloride, and further washed with aqueous hydrochloric acid solution followed by additional washing with organic solvent such as methanol, acetone, etc., followed by drying the resulting product in a drying oven at a temperature in the range of from 50° C. to 110° C.

Analysis of the resulting polymer bound mercapto sulfonamide can be determined by titration of the residual sulfonic acid with excess 0.1 N NaOH, followed by back titration of the remaining NaOH with 0.1 N HCl. This procedure affords the acid milliequivalency of the acid catalyst. The amount of nitrogen present on the catalyst can be obtained by combustion analysis.

With respect to the preparation of bisphenols utilizing the mercapto sulfonamide ion-exchange resin of the present invention, a mixture of phenol and ketone can be heated in the presence of the cation-exchange resin prepared in accordance with the practice of the present invention. There can be utilized about 2 moles of the phenol per mole of the ketone which can be heated at a temperature in the range of from 50° C. to 110° C. with agitation. The ion-exchange resin can be employed at from 0.1% to 10% by weight, based on the weight of the total mixture in instances where a batch process is used. The mole ratio of reactants can vary widely, such as from about 3 to 1 to about 20 to 1 moles of phenol to ketone. It is preferred, however, to use the reactants at a mole ratio of about 4 to 1 to about 12 to 1 moles of phenol to ketone.

One method of recovering the bisphenol reaction product is by crystallizing the product with phenol and then mechanically recovering the bisphenol. Other procedures are, for example, distillation of the reaction mixture to separate the phenol and bisphenol, or by partial distillation to remove the phenol followed by recrystallization of the residual bisphenol using water, methanol, acetonitrile, methylene chloride, or toluene as the solvent.

In order that those skilled in the art will be better able to practice the present invention, the following examples are given by way of illustration and not by way of limitation. All parts are by weight unless otherwise indicated.

EXAMPLE 1

A mixture of 1100 parts of anhydrous chloroform, 262.6 parts of Amberlite-118, a crosslinked sulfonated polystyrene, polymer manufactured by the Rohm & Haas Company and 361.1 parts of chlorosulfonic acid was refluxed with stirring under an atmosphere of nitrogen for a period of three days. The mixture was allowed to cool and the chloroform-chlorosulfonic acid solution was decanted from the remaining resin. The resin was then washed with chloroform. The wet resin was then slowly added to a methanol solution at 5° C. at a rate sufficient to maintain the temperature below 15° C. The resulting mixture was filtered and the resin was washed with cold water, methanol, chloroform, and finally ethylether. After a brief air drying, the resin was dried by azeotropic distillation with heptane, followed by drying in an evacuated oven at 70° C.

A mixture of 0.5205 part of the chlorosulfonated resin, about 50 parts of a 0.10 N-sodium hydroxide solution, and 4.45 parts of tetrahydrofuran was refluxed with stirring under an atmosphere of nitrogen for a period of 3 hours. The mixture was then cooled, filtered and the resin was washed with excess amounts of deionized water. The chlorine content of the resulting resin was then determined by the potentiometric titration using 0.098 N-silver nitrate as the titrant. It was found that the chlorine content of the resin was 15.5% by weight.

There was added 2.7 parts of 2-aminoethyl disulfide (cystamine dihydrochloride), and 25 parts of the above chlorosulfonated polystyrene resin to 350 parts of deionized water which had been preheated to 90° C. The pH of the resulting mixture was adjusted to 9.4 by the addition of sodium carbonate. While heating the reaction mixture to 95° C. additional sodium carbonate was added to the reaction mixture to maintain the pH at 9.4. After about 20 minutes, the pH stabilized and heating was continued for an additional 30 minutes. The resulting cooled ion-exchange resin was removed by filtration and washed with water, followed by methanol.

There was added 5 parts of the above disulfide substituted resin to a solution of about 36 parts of methanol and 5 parts of water. There was then added to the resulting mixture 0.3 part of triphenylphosphine. The resulting mixture was brought to reflux for a period of 4 hours. The solution was allowed to cool. The resin was then washed with methanol, methylene chloride, a 20% sulfuric acid solution in water, acetone, ether, followed by drying it in an evacuated drying oven at 80° C. Based on method of preparation, there was obtained an ion-exchange resin consisting essentially of about 13 mole percent of chemically combined mercapto ethyl amino sulfonamide styryl units and about 87 mole percent of chemically combined sulfonyl styryl units.

EXAMPLE 2

A mixture of 10 parts of phenol, 1 part of acetone, and 2 parts of the ion-exchange catalyst of Example 1 was heated at 70° C. for 1 hour. The mixture was allowed to cool and diluted with acetonitrile followed by filtration and washing the catalyst with acetonitrile. The concentration of the filtrate provided a pale yellow liquid which crystallized on standing. There was obtained a mixture of 98% of para,para-bisphenol-A and about 1.4% of ortho,para-bisphenol-A or a conversion of 66.8%, based on high pressure liquid chromatography.

The same procedure was repeated, except that the ion-exchange resin utilized was produced by neutralizing the sulfonated polystyrene with 2-mercapto ethyl amine as shown by McNutt et al, U.S. Pat. No. 3,394,089. It was found that the percent conversion of the phenol to bisphenol-A was about 40%.

Although the above examples are directed to only a few of the very many variables of the present invention, it should be understood that the present invention is concerned with a much broader variety of ion-exchange resins which can be made by effecting reaction between the amine disulfide of formula (1) and halo sulfonated aromatic organic polymer having chemically combined units of formula (4), followed by the use of a triorganophosphine of formula (5). In addition, the method of the present invention is also broadly directed to the use of such ion-exchange resin to make a broader variety of bisphenols.

What we claim as new and desire to secure by Letters Patent of the United States is:

1. In a method for making bisphenol, based on the reaction between a ketone and a phenol in the presence of an effective amount of a sulfonated polystyrene cation-exchange resin in acid form modified by the neutralization of 5–25% of a cation-exchange capacity with a promoter in the form of an organo mercapto amine whereby the promoter is incorporated onto the cation-exchange resin backbone by an acid-amine salt ionic bond which is susceptible to excessive loss from the cation-exchange resin due to leaching as the result of the degradation of the acid-amine salt ionic bond during the use of the ion-exchange resin in phenol-ketone condensation reaction, the improvement which comprises utilizing as the cation-exchange resin, a sulfonated polystyrene having 5–25% of its cation-exchange capacity occupied by $C_2$–$C_{14}$ organo mercapto amine covalently bonded to the cation-exchange backbone by nitrogen-sulfur linkages.

2. A method in accordance with claim 1, where the bisphenol is bisphenol-A.

* * * * *